United States Patent
Werle et al.

(10) Patent No.: US 6,844,306 B2
(45) Date of Patent: Jan. 18, 2005

(54) WATER-SOLUBLE, CHLORHEXIDINE-CONTAINING COMPOSITIONS AND USE THEREOF

(75) Inventors: Peter Werle, Gelnhausen (DE); Friedhelm Merz, Nierstein (DE); Jolanta Habrich, Hainburg (DE)

(73) Assignee: Degussa AG, Duesseldorf (DE)

( * ) Notice: Subject to any disclaimer, the term of this patent is extended or adjusted under 35 U.S.C. 154(b) by 273 days.

(21) Appl. No.: 09/982,240

(22) Filed: Oct. 19, 2001

(65) Prior Publication Data

US 2002/0072480 A1 Jun. 13, 2002

(30) Foreign Application Priority Data

Oct. 21, 2000 (DE) .......................... 100 52 322

(51) Int. Cl.$^7$ ................................. C11D 1/50
(52) U.S. Cl. ........................................ 510/391
(58) Field of Search .................. 510/131, 132, 510/133, 191, 445, 446, 447, 499, 391

(56) References Cited

U.S. PATENT DOCUMENTS 3,888,947 A   6/1975   Stephenson et al.
4,201,599 A * 5/1980 Morgans ................. 148/6.14 R
4,548,950 A * 10/1985 Baxendale et al. .......... 514/510
5,614,310 A * 3/1997 Delgado et al. .......... 428/316.6
2001/0014653 A1 * 8/2001 Soyer et al. ................. 510/112

FOREIGN PATENT DOCUMENTS

| DE | 34 43 232 |   | 6/1985 |
|----|-----------|---|--------|
| EP | 1 018 337 |   | 7/2000 |
| FR | 2752731   | * | 3/1998 |
| JP | 7-88169   | * | 4/1995 |

* cited by examiner

*Primary Examiner*—John R. Hardee
(74) *Attorney, Agent, or Firm*—Oblon, Spivak, McClelland, Maier & Neustadt, P.C.

(57) ABSTRACT

The invention relates to water-soluble, chlorhexidine-containing compositions having a long shelf life. The compositions are in the form of powder, granules or tablets and consist substantially of (i) a salt of chlorhexidine with 2 moles of a sugar acid and a microbicidally active quaternary ammonium bromide, or of (ii) chlorhexidine, a sugar acid or sugar lactone, with at least 2 moles of sugar acid or sugar lactone being present per mole of chlorhexidine, and a microbicidally active quaternary ammonium bromide. Peferred compositions consist substantially of chlorhexidine digluconate and N-cetyl-N,N,N-trimethylammonium bromide (cetrimide) in a weight ratio of 1:1 to 1:10. The solid compositions are stable, with little or no p-chloroaniline splitting off during storage.

12 Claims, No Drawings

WATER-SOLUBLE, CHLORHEXIDINE-CONTAINING COMPOSITIONS AND USE THEREOF

BACKGROUND OF THE INVENTION

1. Field of the Invention

The invention relates to water-soluble, chlorhexidine-containing compositions and to the use thereof. The compositions contain chlorhexidine in the form of the free base or in the form of a chlorhexidine disalt.

2. Discussion of the Background

Clorhexidine (CHD), chemically identified as 1,1'-hexamethylenebis[5-(p-chlorophenyl)biguanide], is a substance having a strongly basic action with only very low water solubility. By reacting the chlorhexidine base with acids, a large number of salts that are also sparingly water-soluble can be obtained. However, some salts of chlorhexidine with sugar acids are water-soluble. Chlorhexidine base, and especially the water-soluble chlorhexidine digluconate, a salt of D(+)-gluconic acid with chlorhexidine, represent important antibacterial substances for use in both the human and the animal sector. Their low toxicity and compatibility with cationic and non-ionic detergents should be highlighted. Chlorhexidine digluconate (CHD-gluc) is commercially available as a 20 wt. % aqueous solution. Liquid formulations containing chlorhexidine are modified in many different ways and used as an antibacterial additive in cosmetics, for skin disinfection, treatment of wounds, in veterinary medicine as an udder disinfectant, and also for disinfecting surfaces.

CHD gluconate solutions are subject to the requirements of the European Pharmacopoeia or the United States Pharmacopeia with respect to their composition and appearance. One of the purity requirements is the content of p-chloroaniline, which is limited to 500 ppm. In an inversion of the formation of CHD (=CHD base) from hexamethylene-biscyanoguanidine and p-chloroaniline according to the following equation:

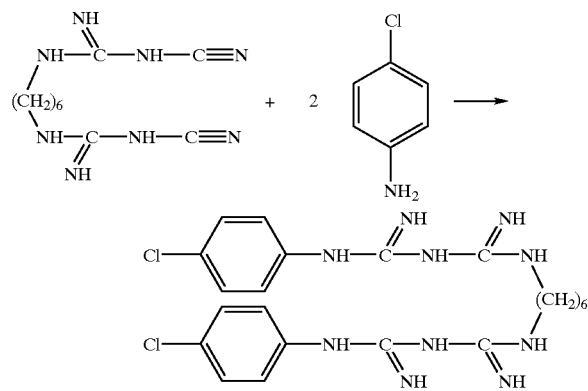

p-chloroaniline can be reversibly split off during the salt formation of the CHD base with D(+)-gluconic acid δ-lactone, the internal ester of D(+)-gluconic acid, in the aqueous phase, and on standing, i.e. storage of these solutions. As the storage period increases, the solutions take on a yellow to brownish discoloration. This decomposition of chlorhexidine digluconate solutions is dependent on the pH of the solution and particularly on the storage temperature. Investigations have shown that, when a 20 wt. % solution of chlorhexidine digluconate is stored at 40° C., the permitted p-chloroaniline values are exceeded after about one month. Even frequently used solutions containing CHD digluconate and other microbicidally active substances are subject to this hydrolysis to varying degrees.

One frequently used combination contains chlorhexidine digluconate and N-cetyl-N,N,N-trimethylammonium bromide (cetrimide) as active substances in dilute aqueous or alcoholic solutions. Even these solutions have inadequate storage stability. Solid compositions containing chlorhexidine or a salt thereof and cetrimide or similar microbicides, which dissolve in water to form a clear solution and are inherently stable even at an elevated storage temperature, have been unknown up to the present.

The object of the present invention is therefore to provide such biocidal mixtures, from which ready-to-use solutions can be obtained by adding water.

SUMMARY OF THE INVENTION

The invention provides a water-soluble, chlorhexidine-containing composition, in the form of a powder, granules or tablets, substantially consisting of:

(i) a salt of chlorhexidine with 2 moles of a sugar acid and a microbicidally active quaternary ammonium bromide, or of (ii) chlorhexidine, a sugar acid or sugar lactone, with at least 2 moles of sugar acid or sugar lactone being present per mole of chlorhexidine, and a microbicidally active quaternary ammonium bromide.

DETAILED DESCRIPTION OF PREFERRED EMBODIMENTS

It has been found that a mixture of solid, powdered chlorhexidine digluconate and cetrimide in different ratios, the mixture optionally having been converted, if necessary, into a form suitable for the application, e.g. granulated, tabulated or pelleted, surprisingly dissolves in water without residues and permits the preparation of ready-to-use solutions or solutions that can be further diluted. This finding was unexpected, since sparingly water-soluble chlorhexidine bromide is often precipitated in a chlorhexidine digluconate solution in the presence of bromide ions.

From the solubility product for chlorhexidine dibromide of $L=9.3\times10^{-8}$ mol$^3$/l$^3$, limiting concentrations for the species present in the solution, diprotonated chlorhexidine (=CHD dication), bromide ion and chlorhexidine dibromide (=CHD dibromide) can be calculated. A saturated chlorhexidine bromide solution should, according to this, contain approximately 1400 mg of chlorhexidine dication and 450 mg of bromide ions per liter. Mixtures of solid chlorhexidine digluconate and substances containing bromide ions, such as cetrimide, should therefore only dissolve in water to a limited extent. Ion concentrations exceeding the maximum values established by the solubility product should lead to precipitations. Surprisingly, however, it has been found that solid mixtures of chlorhexidine digluconate and cetrimide dissolve in water to give a clear solution, without the occurrence of the expected precipitation of CHD dibromide when the solubility product is exceeded.

Compositions according to the invention contain as the chlorhexidine salt a salt of a sugar acid, the salt containing the diprotonated chlorhexidine dication and two acid anions from the sugar acid. In addition to the long known chlorhexidine digluconate, salts of this type are described in EP 1 018 337 A2, the disclosure of which is incorporated by reference herein in its entirety. Preferred salts contain the anion of gluconic acid, especially of D(+)-gluconic acid, lactobionic acid, D-galactonic acid, L-mannonic acid, D-galacturonic acid, D-gulonic acid and α-D-heptagluconic acid. Alternatively, instead of a chlorhexidine salt, the composition can contain a combination of chlorhexidine (free base) and a sugar acid, such as those mentioned above, or lactone thereof, such as D-galactono-γ-lactone, L-mannonic acid-γ-lactone, D-gulono-γ-lactone, D-gluconolactone, δ-gluconolactone, and α-D-heptagluconic acid-γ-lactone, with generally at least two moles of acid or lactone being present per mole of CHD base, but an acid or lactone excess, e.g. up to 100%, especially up to 20%, is possible. Combinations of this type form CHD salts when dissolved in water.

Microbicidally active quaternary ammonium bromides are intended to mean those compounds having at least one medium- to long-chain alkyl or alkenyl residue with 8 to 18 C atoms and up to three identical or different short-chain alkyl residues with 1 to 7 C atoms which, in turn, can additionally contain a hydroxyl and/or halogen group or/and an epoxy group. These are, in particular, ($C_{10}$ to $C_{16}$)alkyl-tri($C_1$ to $C_3$)alkylammonium bromide, particularly preferably N-cetyl-N,N,N-trimethylammonium bromide, which is widely used under the name of cetrimide as a microbicidal active component in disinfectants.

The term "chlorhexidine-containing" means that the composition contains chlorhexidine in the form of the free base or in the form of a chlorhexidine salt, which itself exhibits the diprotonated chlorhexidine dication.

The term "substantially" includes conventional auxiliary substances for microbicidal formulations. Examples of these are surface-active substances, tablet disintegrants, granulating aids and solution aids. These auxiliary substances can be contained in a total quantity of up to 20 wt. %, particularly less than 10 wt. % and preferably up to 5 wt. %, based on the sum of the biocides in the composition in each case.

The microbicidal active components can be present in any weight ratio here. The compositions according to the invention usually contain chlorhexidine in the form of the free base or of the diprotonated dication and a microbicidally active quaternary ammonium bromide, such as cetrimide, in a weight ratio in the range of 1:2 to 1:20, particularly in the range of 1:5 to 1:20, but chlorhexidine or a salt thereof can also be present in excess in relation to the ammonium bromide.

A completely water-soluble 1:1 chlorhexidine gluconate-cetrimide mixture can contain up to about 6 wt. % cetrimide, after dissolving in water, since the concentration of cetrimide that can be tolerated is limited by the restricted water solubility of cetrimide (approx. 67 g/l). With a mixing ratio of CHD or the dication of a salt to cetrimide, as the cetrimide content increases, the concentration of CHD that can be achieved in solution is correspondingly reduced. At a weight ratio of 1:20, therefore, clear solutions can be produced only with a content of about 0.6% CHD dication, as otherwise, cetrimide remains undissolved. However, more highly concentrated solutions can be produced by adding alcohols.

The invention further provides a process for the production of compositions according to the invention. Chlorhexidine and a sugar acid or lactone thereof are mixed in a molar ratio adequate for formation of the disalt, i.e. 1 to at least 2, with the quaternary ammonium bromide, such as in particular cetrimide. Chlorhexidine and the ammonium bromide are preferably used in a weight ratio in the range of 1:2 to 1:20, particularly 1:5 to 1:20. All the ingredients are usefully present in powder form. The mixing can also comprise grinding.

During or after the mixing or grinding, the powdered mixture can be granulated, pastillated or tableted, conventional granulating aids and/or tablet disintegrants optionally also being added. Instead of the combination of chlorhexidine and a sugar acid or lactone thereof, a chlorhexidine salt formed therefrom can be used. Chlorhexidine digluconate and cetrimide are preferably used in a weight ratio of 1:1 to 1:10.

A technically practicable route for the production of powdered chlorhexidine digluconate or other chlorhexidine salts of sugar acid includes cooling a 20 to 40 wt. % aqueous solution of the salt to temperatures of −50 to −80° C. and removing the water by high-vacuum sublimation.

Cetrimide is commercially available as a solid. The mixing of the two components takes place by homogenising in suitable apparatus.

When using chlorhexidine base (a), a sugar acid lactone (b), such as δ-gluconolactone, and cetrimide, no pre-mixing or salt formation of components (a) and (b) is necessary. Used in the correct ratio, a powder that dissolves in water is obtained in this case too. Because of the necessary reaction time of the base and the period of the hydrolysis of the lactone to the free acid, however, such systems require a prolonged dissolving period.

The compositions according to the invention can be used for the preparation of aqueous or aqueous-organic disinfectant solutions. These solutions can contain the final application concentration of both biocidally active components or can be further diluted before application.

Merits of the composition according to the invention include high storage stability, since the water that impairs the stability is only added prior to application; ready obtainability and variability of the compositions; and ready availability of disinfectant solutions with different contents of active substance.

EXAMPLES

The following examples are intended to describe the invention in more detail.

Example 1

Production of Solid Chlorhexidine Digluconate 200 g of a 20% (100 g of a 40%) chlorhexidine digluconate solution are placed in a 1 liter flask and frozen out in a mixture of solid carbon dioxide in ethanol. The cold, crystalline material, at approximately −78° C., is then freed from water in high-vacuum sublimation apparatus. Chlorhexidine gluconate remains as a completely colourless, powdered product. Residual water content is less than 1%. On heating, it begins to sinter markedly from approximately 60° C., and a clear melt is present at 85 to 90° C.

Examples 2 to 4

As shown in Table 1, in Examples 2a to 4a chlorhexidine digluconate (=CHD-gluc)/cetrimide mixtures were prepared from chlorhexidine digluconate and cetrimide in the ratios 1:1, 1:5 and 1:10. The solids were weighed into screw-cap jars and then homogenised for 30 minutes.

In Examples 2b to 4b, instead of solid CHD digluconate, a mixture of CHD base and δ-gluconolactone was used.

TABLE 1

| Example | CHD gluc (g) | Cetrimide (g) | CHD base (g) | δ-Glucolactone (g) |
|---|---|---|---|---|
| 2a | 15 | 15 | — | — |
| 2b | — | 15 | 10.9 | 4.1 |
| 3a | 15 | 75 | — | — |
| 3b | — | 75 | 10.9 | 4.1 |
| 4a | 15 | 150 | — | — |
| 4b | — | 150 | 10.9 | 4.1 |

Example 5

Solutions of the mixtures of the compositions of Examples 2b to 4b were prepared by introducing the desired quantity of active substance into water. The following Table 2 gives the dissolving periods for the preparation of solutions with different concentrations.

TABLE 2

| Concentration of CHD gluconate | Dissolving period in minutes Mixing ratio (CHD base + δ-gluconolactone):Cetrimide | | | | | |
|---|---|---|---|---|---|---|
| | 1:1 | | 1:5 | | 1:10 | |
| (%) | 20° C. | 60° C. | 20° C. | 60° C. | 20° C. | 60° C. |
| 0.5 | 50–60 | 14–18 | 60 | 8–10 | 75 | 7 |
| 1 | 35–40 | 10–14 | 200 | 10–14 | 240 | 14 |
| 5 | 25–30 | 8–10 | — | | — | |

When solid CHD digluconate, obtained by freeze-drying, is used, the dissolving periods are substantially reduced. At room temperature they are in the range of about 5 minutes, the dissolving period being dependent on the rate of dissolution of the cetrimide component.

At concentrations of 1.0% CHD digluconate in the solution and a CHD digluconate/cetrimide ratio of 1:1, 10 g of CHD gluconate or 5630 mg of CHD base and 2090 mg of bromide ions are present in the solution. Nevertheless, no CHD dibromide is precipitated. An addition of alcohols (n-propanol; isopropanol; ethanol) in the range of 1 to 2% has a stabilizing effect. This stabilizing is useful with higher concentrations of active substances and a low storage temperature. The solid mixtures according to the invention, preferably in the form of powder, tablets or granules, have a long shelf life and no p-chloroaniline is split off even at higher temperatures.

Example 6

Table 3 shows a comparison of the splitting off of p-chloroaniline in the solid mixture of CHD digluconate and cetrimide according to the invention in a weight ratio of 1:1 and in a 4% aqueous solution thereof at a storage temperature of 40° C.

TABLE 3

| Storage period | Powder | Solution |
|---|---|---|
| Start | <10 | <10 |
| 1 month | <10 | 23 |
| 3 months | <10 | 38 |
| 6 months | <10 | 55 |

The disclosure of the priority document, German patent application no. 100 52 322.6, filed Oct. 21, 2000, is incorporated by reference herein in its entirety.

What is claimed is:

1. A chlorhexidine composition comprising:

chlorhexidine and Δ-gluconolactone, wherein the chlorhexidine and Δ-gluconolactone are present in a molar ratio of 1:2 to 1:2.2, and a microbicidally active quaternary ammonium bromide comprising cetramide;

wherein said chlorhexidine composition is water soluble and in the form of a powder, granule or tablet.

2. The chlorhexidine composition of claim 1 in the form of a powder.

3. The chlorhexidine composition of claim 1 in granular form.

4. The chlorhexidine composition of claim 1 in the form of a tablet.

5. The chlorhexidine composition of claim 1, wherein the microbicidally active quaternary ammonium bromide consists of cetramide.

6. The chlorhexidine composition of claim 1, wherein the chlorhexidine and the cetrimide are in a weight ratio ranging from 1:2 to 1:20.

7. The chlorhexidine composition of claim 1, wherein the chlorhexidine and the cetrimide are in a weight ratio ranging from 1:5 to 1:20.

8. A method for forming an aqueous or aqueous-organic solution comprising:

mixing the chlorhexidine composition of claim 1 with a liquid containing water to form an aqueous or an aqueous-organic solution.

9. The method of claim 8, wherein the liquid further comprises up to 2% of an alcohol selected from the group consisting of n-propanol, isopropanol, and ethanol.

10. An aqueous or aqueous-organic solution produced by the method of claim 8.

11. A method for disinfecting a surface comprising:

applying the solution of claim 10 to a surface.

12. A method for making a chlorhexidine composition comprising:

mixing chlorhexidine and Δ-gluconolactone, wherein the chlorhexidine and Δ-gluconolactone are present in a molar ratio of 1:2 to 1:2.2, and a microbicidally active quaternary ammonium bromide which comprises cetramide to form a mixture, and optionally pistillating, granulating, or tableting said mixture to form a powder, granule or tablet.

* * * * *